(12) United States Patent
Ihn

(10) Patent No.: US 8,042,397 B2
(45) Date of Patent: Oct. 25, 2011

(54) DAMAGE VOLUME AND DEPTH ESTIMATION

(75) Inventor: Jeong-Beom Ihn, Bellevue, WA (US)

(73) Assignee: The Boeing Company, Chicago, IL (US)

( * ) Notice: Subject to any disclaimer, the term of this patent is extended or adjusted under 35 U.S.C. 154(b) by 21 days.

(21) Appl. No.: 12/628,760

(22) Filed: Dec. 1, 2009

(65) Prior Publication Data
US 2010/0319455 A1 Dec. 23, 2010

Related U.S. Application Data

(63) Continuation-in-part of application No. 12/103,118, filed on Apr. 15, 2008, which is a continuation-in-part of application No. 11/749,539, filed on May 16, 2007, now Pat. No. 7,891,247.

(51) Int. Cl.
*G01N 29/04* (2006.01)
(52) U.S. Cl. .............. 73/603; 73/600; 73/602; 73/606; 73/618
(58) Field of Classification Search .............. 73/603, 73/600, 602, 606, 618
See application file for complete search history.

(56) References Cited

U.S. PATENT DOCUMENTS

| | | | |
|---|---|---|---|
| 4,866,614 A | 9/1989 | Tam | |
| 5,031,154 A * | 7/1991 | Watanabe | 367/8 |
| 5,628,320 A * | 5/1997 | Teo | 600/443 |
| 6,672,165 B2 * | 1/2004 | Rather et al. | 73/603 |
| 7,149,337 B2 * | 12/2006 | Michaelis et al. | 382/141 |
| 7,502,102 B2 * | 3/2009 | Johannesson et al. | 356/237.2 |
| 7,679,751 B1 * | 3/2010 | Kablotsky | 356/445 |
| 2003/0009300 A1 | 1/2003 | Giurgiutiu | |
| 2008/0283332 A1 | 11/2008 | Ihn | |
| 2009/0032329 A1 | 2/2009 | Ihn | |
| 2009/0192729 A1 | 7/2009 | Pado et al. | |

OTHER PUBLICATIONS

European Search Report mailed Mar. 18, 2011 for Application No. 10183287.9-2204.

* cited by examiner

*Primary Examiner* — Jacques M Saint Surin
(74) *Attorney, Agent, or Firm* — Caven & Aghevli LLC

(57) ABSTRACT

In one embodiment, a system to characterize an anomaly in a laminate structure comprises a plurality of actuators to generate a wave signal into a structure being evaluated, a plurality of sensors to collect scattered wave data caused by energy of the wave signal being at least partially reflected or scattered by an anomaly, and a structural health monitoring unit. In some embodiments the structural health monitoring unit executes a scatter imaging algorithm to generate three dimensional image data for the anomaly from the scattered wave data, extracts a scatter volume from the from the scattered wave data, and generates a damage volume estimate and a damage depth estimate from the scattered wave data. Other embodiments may be described.

21 Claims, 13 Drawing Sheets

DAMAGE VOLUME AND DEPTH ESTIMATION

RELATED APPLICATIONS

This application is a continuation-in-part of application Ser. No. 12/103,118, filed Apr. 15, 2008, entitled "IMAGING AN ANOMALY USING BACKSCATTERED WAVES," which is a continuation-in-part of application Ser. No. 11/749,539, filed May 16, 2007 now U.S. Pat. No. 7,891,247, entitled "METHOD AND SYSTEM FOR DETECTING AN ANOMALY AND DETERMINING ITS SIZE," the disclosures of which are incorporated herein by reference in their respective entirety.

BACKGROUND

The present invention relates to detecting anomalies in a structure, such as an aircraft or other structure, and more particularly to a method and system for characterizing an anomaly, such as a delamination or other defect, and estimating or determining its size, shape and location.

New, lightweight composite materials and designs are being used more extensively in the aerospace industry for commercial aircraft and other aerospace vehicles, as well as in other industries. The structures using these composite materials may be formed using multiple plies or layers of material that may be laminated together to form a lightweight, high strength structure. Similar to traditional materials, these structures may be subject to extreme stresses, such as during flight operations for aerospace vehicles or other operations, or damage from an impact or other cause. The multiple plies of material can separate or become delaminated as a result of these stresses or impact. As new and traditional materials are being designed in more optimized manner, there is also the need in the aerospace industry to quickly identify and maintain all structures with better efficiency—improving the dispatch reliability and increasing the in-service use of aircraft and any other similar expensive equipment. As such, there is a need to quantify damage or delamination size in plate-like structures using permanently attached piezoelectric actuators/sensors but such efforts have failed to successfully demonstrate feasibility of actual implementation on real aircraft structures due to heavy dependency on simplified analytical models and lack of simple but robust interpretation techniques relating complex signal responses to damage information and the like. Accordingly, a means to non-destructively inspect for damage and monitor the health or condition of such structures and to determine or measure a size, shape and location of any anomalies or delaminations is needed. Similar needs also exist and similar benefits may be realized for more traditional materials such as metallic structures requiring quick, frequent or infrequent inspections, periodically over time to status the known state of the structure's health.

SUMMARY

In one aspect, the subject matter described herein relates to a method to characterize an anomaly in a laminate structure using a distribution of actuators and sensors. In one embodiment the method comprises generating a series of wave signals in the structure from the distribution of actuators, collecting, in the sensors, scattered wave data caused by the series of generated wave signals impacting the anomaly, executing a scatter imaging algorithm to generate three dimensional image data for the anomaly from the scattered wave data, extracting a scatter volume from the from the scattered wave data and generating a damage volume estimate and a damage depth estimate from the scattered wave data.

In another aspect, the subject matter described herein relates to a system to characterize an anomaly in a laminate structure. In one embodiment the system comprises a plurality of actuators to generate a wave signal into a structure being evaluated, a plurality of sensors to collect scattered wave data caused by energy of the wave signal being at least partially reflected or scattered by an anomaly, and a structural health monitoring unit. In some embodiments the structural health monitoring unit executes a scatter imaging algorithm to generate three dimensional image data for the anomaly from the scattered wave data, extracts a scatter volume from the from the scattered wave data, and generates a damage volume estimate and a damage depth estimate from the scattered wave data.

Other aspects and features of the present invention, as defined solely by the claims, will become apparent to those ordinarily skilled in the art upon review of the following non-limited detailed description of the invention in conjunction with the accompanying figures.

BRIEF DESCRIPTION OF THE DRAWINGS

The detailed description is described with reference to the accompanying figures.

DETAILED DESCRIPTION

In the following description, numerous specific details are set forth to provide a thorough understanding of various embodiments. However, it will be understood by those skilled in the art that the various embodiments may be practiced without the specific details. In other instances, well-known methods, procedures, components, and circuits have not been illustrated or described in detail so as not to obscure the particular embodiments.

Figure 1:
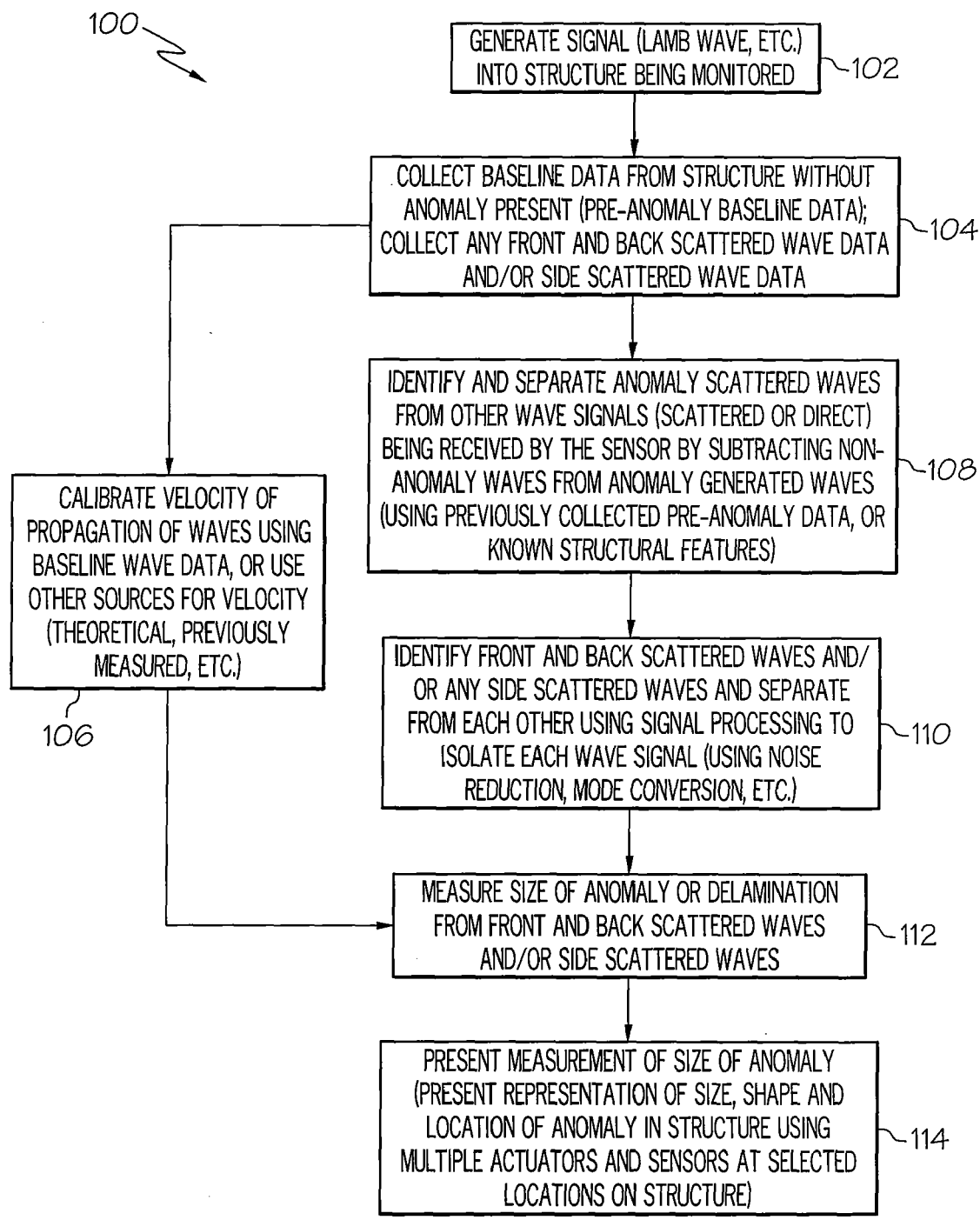
FIGS. 1 is a flow chart of an example of a method for detecting and determining the size of an anomaly in a structure in accordance with an embodiment of the present invention.
Figure 2:
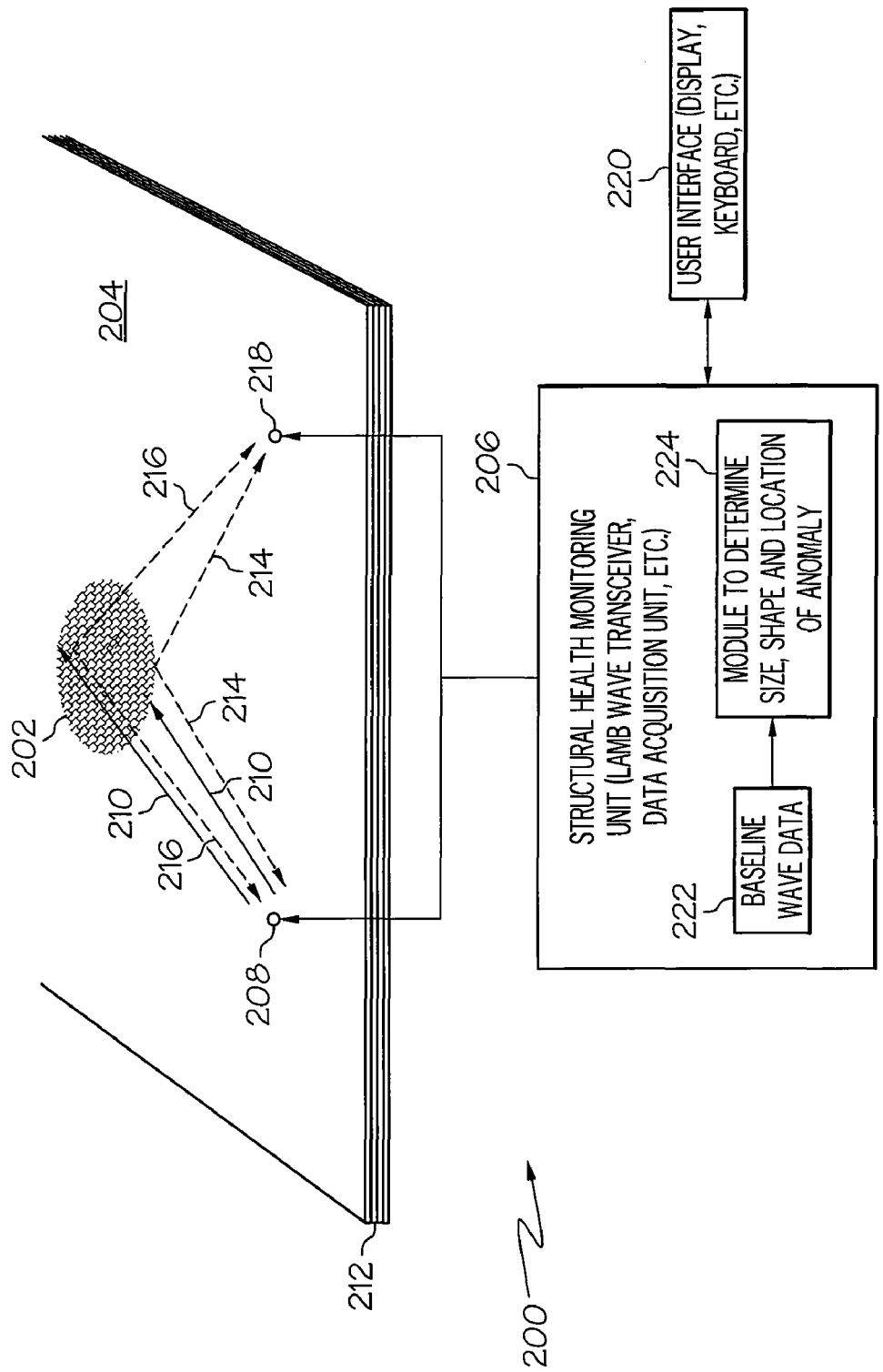
FIG. 2 is a block diagram of an exemplary system for detecting and determining the size of an anomaly in a structure in accordance with an embodiment of the present invention.

FIGS. 1 is a flow chart of an example of a method 100 for detecting and determining the size of an anomaly in a structure in accordance with an embodiment of the present invention. In block 102, a signal, pulse wave, lamb wave or similar wave signal may be generated and directed into a structure being monitored. Lamb waves may be used for detecting and determining the size of an anomaly because they are similar to longitudinal waves and include compression and rarefraction but are bounded by the surface of the structure into which they are transmitted causing a wave-guide effect. For easier and more robust imaging process, a single mode of Lamb waves or similar pulse wave (i.e. a0 fundamental asymmetric mode or s0 fundamental symmetric mode) may be injected into a structure Referring also to FIG. 2, FIG. 2 is a block diagram of an exemplary system 200 for detecting and determining the size of an anomaly 202 in a structure 204 in accordance with an embodiment of the present invention. A structural health monitoring unit 206 may be used to generate the signal, pulse wave, or other wave signal, and an actuator or combination actuator and sensor 208 may generate, transfer or direct the wave signal, illustrated by arrow 210 in FIG. 2, into the structure 204 or object being monitored. The structural health monitoring unit 206 may be a lamb wave generator or transceiver, data acquisition unit capable of transmitting and receiving signals for structural health monitoring as described herein or the like.

The actuator or combination actuator-sensor 208 may be an electromechanical actuator/sensor capable of generating or directing a signal for structural health monitoring, such as a lamb wave or similar signal or wave, into the structure 204. An example of the actuator or combination actuator-sensor 208 may be a piezoelectric actuator/sensor or similar device attachable to the structure 204.

The structure 204 or object may be formed by a plurality 212 of plies or layers of composite material, a solid metallic material, or other similar solid or laminated material. The structure 204 or object may be a vehicle, such as an aerospace vehicle, terrestrial vehicle, watercraft, civil structure, such as a bridge, building or other structure, or any object were monitoring the structural health or condition is desired.

Referring back to FIG. 1, in block 104, any front and back scattered wave data caused by the wave signal 210 impacting an anomaly, such as anomaly 202, crack or delamination in the example of FIG. 2, may be collected. The front and back scattered waves or wave data are illustrated in FIG. 2 by broken or dashed arrows 214 and 216, respectively. The front and back scattered wave data 214 and 216 or signal may be collected by the combination actuator-sensor 208 if the actuator-sensor 208 is self-sensing. The front and back scattered wave data 214 and 216 or signal may also be collected by a sensor 218 capable of receiving such wave data or pulses and transmitting the received or collected wave data to the structural health monitoring unit 206 for analysis to measure the size of the anomaly 202 or delamination. The sensor 218 may also be an electromechanical device, such as a piezoelectric sensor or similar device capable of sensing the front and back scattered waves 214 and 216. In another embodiment of the present invention, side scattered waves or wave data may be collected or may be collected in addition to the back and front scatter waves. An example of collecting side scattered waves will be described with reference to FIG. 5.

The system 200 may include actuators 208 without a sensing capability and sensors 218 in what may be referred to as a pitch-catch arrangement or pitch-catch actuators/sensors and may operate in a pitch-catch mode. The actuators 208 may transmit or pitch wave signals 210 into the structure 204 and the sensors 218 may receive or catch any front and back scattered wave data 214 and 216 from any anomaly 202. Alternatively, as described above, the devices 208 and 218 may both be combination actuator and sensor devices for both transmitting the wave signal 210 and receiving the front and back scattered wave data 214 and 216 and sending the data to the structural health monitoring unit 206 to determine or measure the size of the anomaly 202. The arrangement may be referred to as a pulse-echo arrangement or pulse-echo actuators/sensors and may operate in a pulse-echo mode. Any combination of multiple pitch-catch actuators/sensors or pulse-echo actuators/sensors that may be positioned at predetermined locations to measure the size and location of the anomaly 202. The combination actuator and sensor devices may also operate in a pitch-catch mode.

In accordance with another embodiment of the present invention, a plurality of actuators or combination actuator-sensors, similar to actuator/sensor 208, and a plurality of sensors, similar to sensor 218, may be positioned at selected locations on the structure 204 relative to one another to measure the size, shape and location of any anomaly or delamination in the structure 204.

Also in block 104 of FIG. 1, baseline wave data for the structure 204 may also be collected. The baseline wave data may be collected (a) before the structure 204 or object is placed in service, (b) at some point in time before beginning a structural health monitoring program on the structure 204, or (c) anytime during the monitoring process before the damage anomaly is created.

Figure 3:
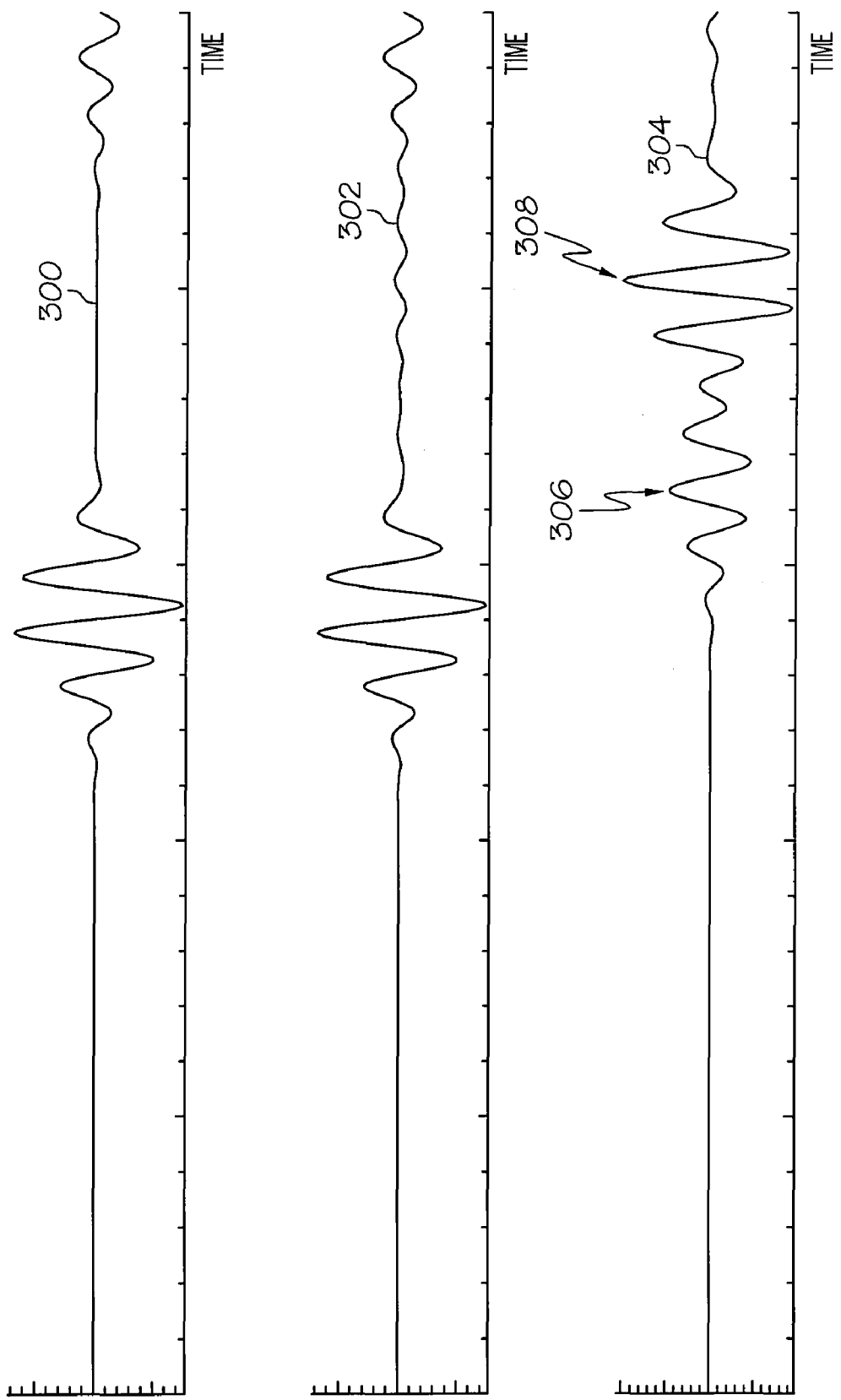
FIG. 3 is an illustration of waveforms for detecting and determining the size of an anomaly in a structure in accordance with an embodiment of the present invention.

In block 106, a velocity of propagation of waves or signals in the structure 204 may be calibrated using the baseline wave data or other sources for velocity, such as theoretical velocity in the particular structure, previously measured velocity in the structure 204 or similar structures or other sources for velocity. The calibrated velocity of propagation of the waves may be used in measuring the size of any anomaly or delamination from the front and back scattered wave data 214 and 216 as described herein. An example of a baseline waveform 300 is illustrated in FIG. 3. FIG. 3 also illustrates an example of a waveform 302 illustrating detection of an anomaly and a waveform 304 illustrating front scattered wave data 306 and back scattered wave data 308.

In block 108, signal processing may be performed on the front and back scattered wave data 214 and 216 using the collected baseline wave data for the structure 204. The scattered waves 214 and 216 induced by the anomaly 202 can be decoupled or separated from any other waves, such as directly transmitted waves from the actuator 208 to sensor 218 and/or other possible reflected waves from any structural boundaries present in the structure 204, by subtracting other reflected waves that are not being reflected from the anomaly 202. One method to do this is by subtracting post damage data from pristine (baseline) wave data.

In block 110, the front and back scattered waves 214 and 216 (and/or side scattered wave waves in other embodiments of the present invention) may be separated or separately identified. The front and back scattered waves 214 and 216 may be separated or identified using signal processing to isolate each wave signal. Examples of signal processing techniques that may be used may include mode decomposition or mode conversion, noise cancellation or reduction or other known signal processing techniques. Applying mode decomposition to the reflected wave signals will help decompose the combined scatter wave which consists of both front scatter and back scatter into individual components that can then be identified into front scatter and back scatter components and the individual time of flight for each wave and be uniquely measured. Other signal processing techniques such as noise cancellation can also be used to more clearly identify the true front scatter and back scatter waves signals.

In block 112, the size of the delamination or other anomaly may be measured from the front and back scattered wave data 214 and 216 (and/or side scattered wave data in other embodiments of the present invention). In an embodiment of the present invention, the size of the delamination or anomaly may be measured based on a difference in arrival time of the front and back scattered wave data 214 and 216 at the sensors 208 and 218 or a Time-of-Flight (TOF) of the wave and based on a calibrated velocity of the wave propagation (V) in the structure 204. The TOF may be defined as the time from when a signal or wave is transmitted and the front and back scattered waves are respectively received. Examples of measuring damage size for different actuator/sensor configurations based on the measured Time-of-Flight information of the back scattered wave (TOFb), the measured Time-of-Flight information of the front scattered (TOFf) and the calibrated velocity V within the structure will be described with reference to FIGS. 4-6.

In block 114, the measurement of the size of the delamination or other anomaly may be presented to a user. The size of the delamination or other anomaly may be presented on a user interface 220 (FIG. 2), such as a display. The user interface 220 may also include a keyboard, computer pointing device or other means for interfacing with and controlling operation of the structural health monitoring unit 206.

Also in block 114, in another embodiment of the present invention, a representation of the measured size, shape, and location of the delamination or other anomaly may be presented. Similar to that previously describe, multiple actuators and sensors may be attached or mounted to a structure at selected locations on the structure. The multiple actuators may send wave signals into the structure. The sensors may receive front and back scattered wave data from any anomaly in the structure to measure and present the representation of the measured size, shape and location of the anomaly. An example of a configuration operable in either a pitch-catch mode or a pulse-echo mode for detecting any anomaly and measuring the anomaly's size and shape will be described with reference to FIGS. 7A and 7B.

Referring again to FIG. 2, the structural health monitoring unit 206 may include a data storage element 222 to store the baseline wave data and any other data for analyzing the front and back scatter wave data 214 and 216. The structural health monitoring unit 206 may also include a module 224 to determine the size of the anomaly 202 or delamination. In another embodiment of the present invention the module 224 may be adapted to determine the size, shape and location of the anomaly if multiple actuators and sensors are used similar to that previously described. The elements of the method 100 may be embodied in the module 224.

Figure 4:
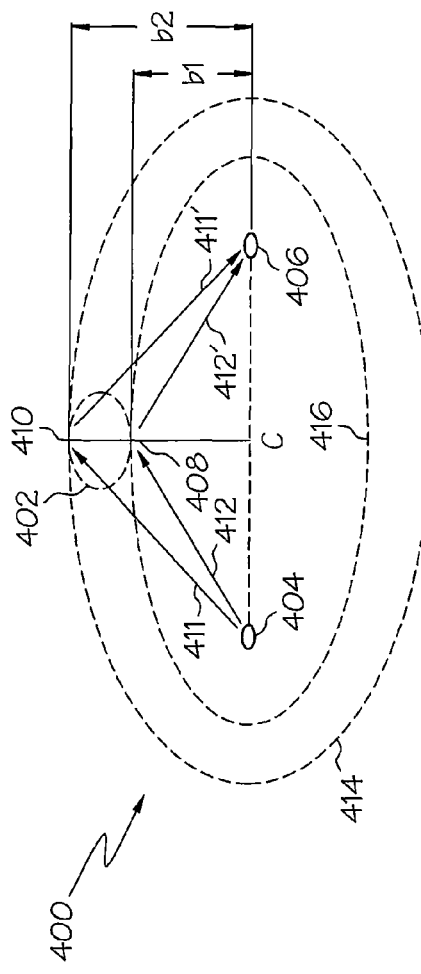
FIG. 4 illustrates an example of a pitch-catch actuator-sensor configuration for detecting and determining the size of any anomaly in a structure when the anomaly is not in a direct path between an actuator and a sensor in accordance with an embodiment of the present invention.

FIG. 4 illustrates an example of a pitch-catch actuator-sensor configuration 400 for detecting any anomaly 402 or damage in a structure and determining the size of the anomaly 402 when the anomaly 402 is not in a direct path between an actuator 404 and a sensor 406 in accordance with an embodiment of the present invention. The size of the anomaly or damage may be determined by equation 1:

$$D = b_2 - b_1 = \sqrt{\left(\frac{1}{2}TOF_b \cdot V\right)^2 - c^2} - \sqrt{\left(\frac{1}{2}TOF_f \cdot V\right)^2 - c^2} \quad \text{Eq. 1}$$

In equation 1, D is the distance between the front boundary 408 and the back boundary 410 of the anomaly as represented by the difference between b1 and b2, the respective distances from the actuator 404 and sensor 406 and the front and back boundaries 408 and 410 or edges of the anomaly 402. TOFb is the Time-of-Flight of a wave signal represented by arrow 411 in FIG. 4 from the actuator 404 to the sensor 406 scattered from the back boundary 410 of the anomaly 402 as represented by arrow 411'. TOFf is the Time-of-Flight of the wave signal represent by arrow 412 from the actuator 404 to the sensor 406 scattered from the front boundary 408 of the anomaly as represented by arrow 412'. V is the velocity of the wave signal propagating through the material and may be the calibrated velocity of the wave or signal in the particular material or structure. Equation 1 assumes an isotropic structure or material and therefore V is constant. The V may be described as being an angle dependent variable in the case of an anisotropic structure. Accordingly, V may vary with angle of the actuator 404 and sensor 406 relative to the anomaly 402 in an anisotropic structure. Module 224 in FIG. 2 may be adapted or modified to compensate for the structure under evaluation being anisotropic. In equation 1, the variable c represents the distance between the actuator 404 and sensor 406.

The substantially elliptically shaped broken or dashed lines 414 and 416 illustrate boundaries of an area associated the actuator 404 and sensor 406 within which any anomaly or damage may be detected and its size determined by the actuator 404 and sensor 406 operating in the pitch-catch mode, as described above, wherein the actuator 404 generates a wave or signal and the sensor 406 senses any of the wave signal scattered by the boundaries of the anomaly 402 or delamination.

Figure 5:
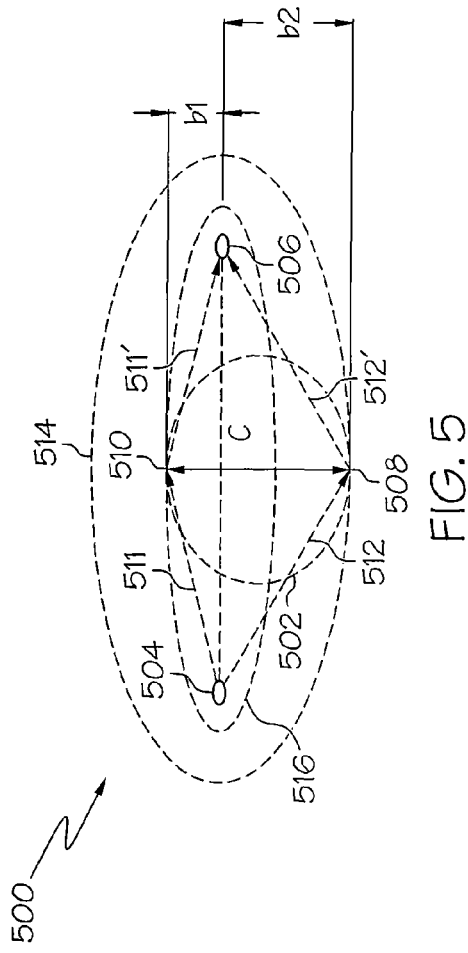
FIG. 5 illustrates an example of a pitch-catch actuator-sensor configuration for detecting and determining the size of any anomaly in a structure when the anomaly is on a direct path between an actuator and a sensor in accordance with an embodiment of the present invention.

FIG. 5 illustrates an example of a pitch-catch actuator-sensor configuration 500 for detecting and determining the size of any anomaly 502 in a structure when the anomaly 502 is on a direct path between an actuator 504 and a sensor 506 in accordance with an embodiment of the present invention. The size of the anomaly 502 or damage may be determined by equation 2:

$$D = b_2 + b_1 = \sqrt{\left(\frac{1}{2}TOF_b \cdot V\right)^2 - c^2} + \sqrt{\left(\frac{1}{2}TOF_f \cdot V\right)^2 - c^2} \quad \text{Eq. 2}$$

The elements of equation 2 are the same as those described with respect to equation 1 above. Equation 2 assumes the structure is isotropic and therefore V will be constant. The velocity V may vary with an angle of the anomaly 502 relative to the actuator 504 and sensor 506 in anisotropic structures.

The broken or dashed lines 514 and 516 illustrate boundaries of an area associated the actuator 504 and sensor 506 where any anomaly or damage may be detected and its size measured by the actuator 504 and sensor 506 operating in the pitch-catch mode similar to that previously described. The paths 511 and 512 represent a signal being sent from the actuator 504. The paths 511' and 512' represent the signal being scattered from respective sides 510 and 508 of the anomaly 502, and being received at the sensor 506. In this scenario, the scatter of primary interest is scattered from the sides 508 and 510 of the anomaly 502.

Figure 6:
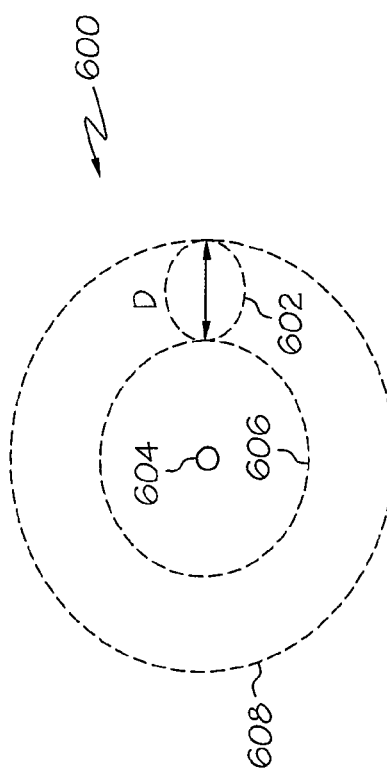
FIG. 6 illustrates an example of a pitch-catch actuator-sensor configuration for detecting and determining the size of any anomaly in a structure when the anomaly is on a direct path between an actuator and a sensor in accordance with an embodiment of the present invention.

FIG. 6 illustrates an example of a pulse-echo (self-sensing) configuration 600 for detecting and measuring the size any anomaly 602 in a structure in accordance with an embodiment of the present invention. At least one device 604 or combination actuator-sensor device that is capable of both generating a wave signal and receiving back scattered wave data may be provided. The size of the anomaly 602 may be determined by equation 3:

$$D = \frac{1}{2}(TOF_b - TOF_f) \cdot Vg \quad \text{Eq. 3}$$

The elements of equation 3 may be the same as those in Equations 1 and 2. The velocity V may vary with an angle relative to the device 604 and the anomaly 602 in an anisotropic structure. The broken or dashed lines 606 and 608 illustrate boundaries of areas associated the device 604 where any anomaly or damage may be detected and its size measured by the device 604 operating in the pulse-echo mode.

Figure 7B:
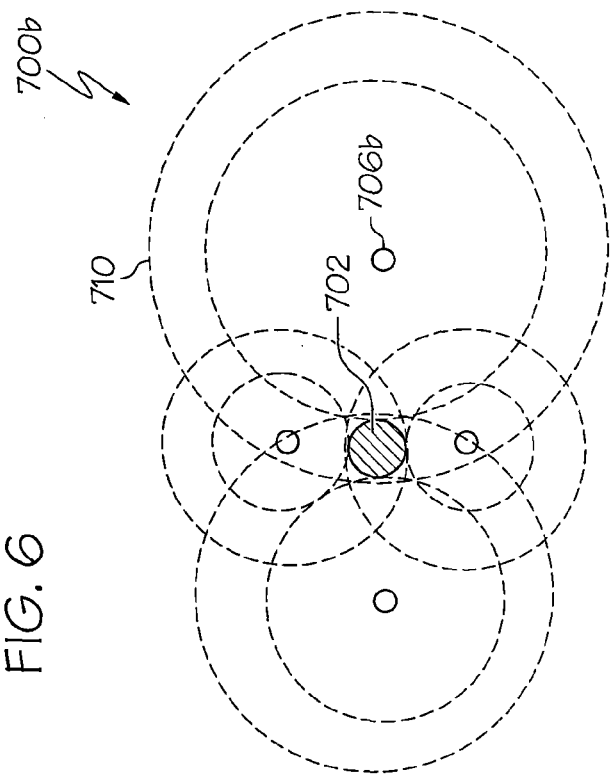
FIGS. 7A and 7B illustrate an example of a sensor-actuator configuration operable in either a pitch-catch mode (FIG. 7A) or a pulse-echo mode (FIG. 7B) for detecting any anomaly and determining the anomaly's size and shape in accordance with an embodiment of the present invention.
Figure 7A:
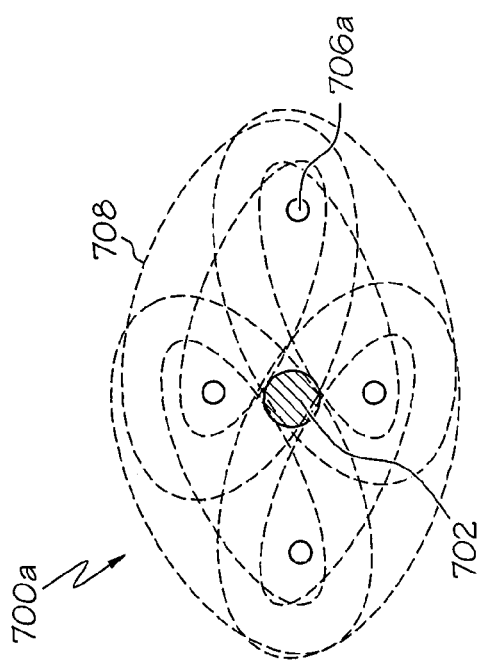

FIGS. 7A and 7B illustrate an example of a configuration 700a and 700b operable in either a pitch-catch mode (FIG. 7A) or a pulse-echo mode (FIG. 7B) for detecting any anomaly 702 and determining or measuring the anomaly's size and shape in accordance with an embodiment of the present invention. The configuration 700 may include multiple devices 706 or combination actuators/sensors capable of both generating a signal or wave and receiving front and back scattered waves or data from any anomaly 702. The devices 706 may also be separate actuators for generating a signal or wave and sensors for receiving the front and back scattered wave data. The devices 706 or separate actuators and sensors may be positioned at predetermined locations on an object to be tested or evaluated.

In FIG. 7A the devices 706a may be operated in a pitch-catch mode or configuration similar to that previously described. In the pitch-catch mode, selected devices 706a may generate or pitch a wave signal and other devices 706a may receive or catch any front and back scattered waves or data from any anomaly 702 or damage. The substantially elliptically shaped broken or dashed lines 708 in FIG. 7A illustrate boundaries of areas associated with each device 706a where any anomaly or damage may be detected and its size determined by the respective device 706a in the configuration 700a operating in the pitch-catch mode.

In FIG. 7B, the devices 706b may be operated in a pulse-echo mode or configuration similar to that previously described. In the pulse-echo mode, each device 706b may generate or pulse a wave or signal and the same device 706b may also receive any front and back scattered waves or data from any anomaly 702. The substantially circular broken or dashed lines 710 associated with each device 706b in FIG. 7B illustrate boundaries of areas where any anomaly or damage may be detected by the respective devices 706b in the configuration 700b operating in the pulse-echo mode. Damage volume may also be determined when multiple devices 706 or actuator-sensors are used by utilizing multiple scattered wave data and scatter imaging techniques.

Figure 8:
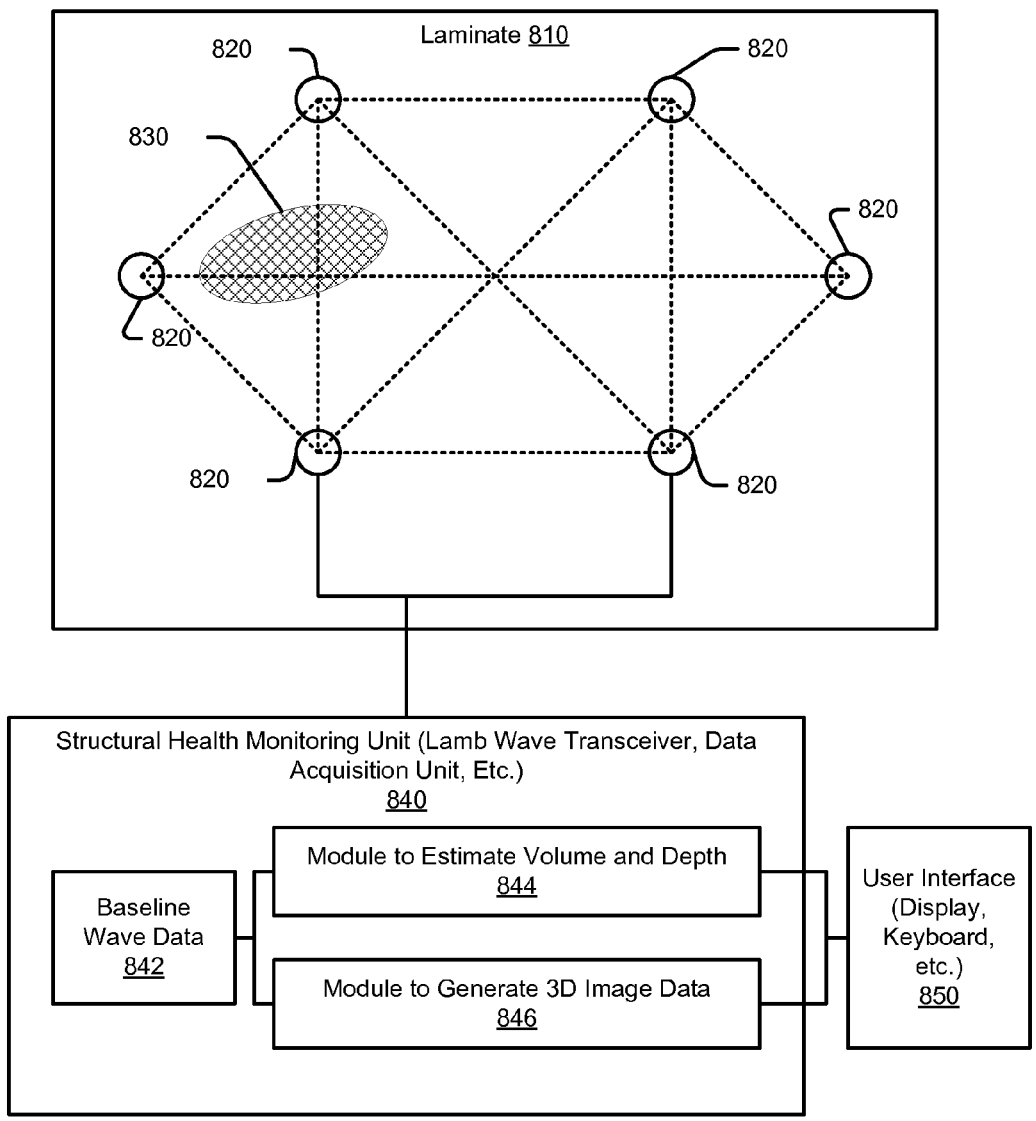
FIG. 8 is a schematic, plane view illustration of a system to characterize damage to a laminate comprising a pitch-catch actuator-sensor configuration which may be used to determine a volume and depth of damage to the laminate, according to embodiments.

In some embodiments a system as described herein may implement methods to characterize, e.g., to assess at least one of a volume or a depth of damage, to a laminate structure. One such system is explained with continued reference to FIGS. 1-7 and with reference to FIGS. 8-15. FIG. 8 is a schematic, plane view illustration of a system to characterize damage to a laminate comprising a pitch-catch actuator-sensor configuration which may be used to determine a volume and depth of damage to the laminate, according to embodiments. Similarly, FIG. 9 is a schematic, cross-sectional view illustration of the laminate depicted in FIG. 8 and illustrating a damage profile from an impact, according to embodiments.

Figure 9:
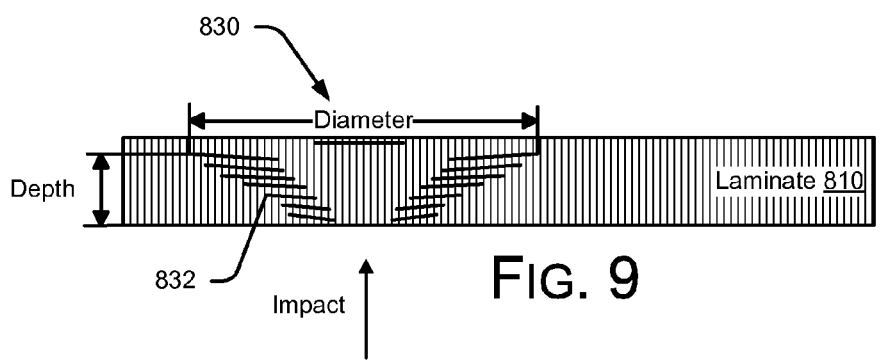
FIG. 9 is a schematic, cross-sectional view illustration of the laminate depicted in FIG. 8 and illustrating a damage profile from an impact, according to embodiments.

Referring now to FIGS. 8 and 9, in one embodiment a laminate structure 810 may comprise an array of sensors 820 disposed on the surface of the laminate 810. As described above with reference to FIG. 1, the sensors 820 may comprise both an actuator which generates a signal to be transmitted through the laminate 810 and a sensor which collects signals transmitted through the laminate. In some embodiments the transducers may be embodied as piezoelectric transducers, which can function both as a transmitter and as a receiver.

In the embodiment depicted in FIG. 8 the transducer elements are arranged in a hexagonal configuration. However, other configurations may be used. In practice, a large laminate structure 810 may comprise an array of sensors 820 spread across the surface of the laminate 810. The entire array of sensors 820 or a subset thereof may be used to assess at least one of a volume or a depth of damage to a laminate structure.

In the embodiment depicted in FIGS. 8 and 9, the laminate structure 810 has an anomaly 830 which may have been created by an impact with an object. By way of example, in some embodiments the laminate 810 may be used as a structural component of a vehicle, e.g., an aircraft, a motor vehicle, or a seaborne vehicle. The laminate structure may have received an impact as indicated in FIG. 9. The impact creates an anomaly 830 in which the laminate structure 810 may comprise internal damage, indicated by the cone-shaped dark lines 832 in the laminate structure. The internal damage may not be visible by inspecting the outer surface of the laminate 810.

As described above with reference to FIG. 2, in some embodiments the plurality of sensors 820 may be a part of a system to characterize an anomaly in the laminate structure 810. In that regard, the various sensors 820 may be connected to a structural health monitoring unit 840. The structural health monitoring unit 830 comprises a module which comprises baseline wave data 842, a module to estimate a volume and depth 844 of an anomaly 830, and a module to generate a 3D image data of an anomaly 830. The various components of the system 840 may be embodied as described with respect to the analogous components depicted in FIG. 2.

Figure 10:
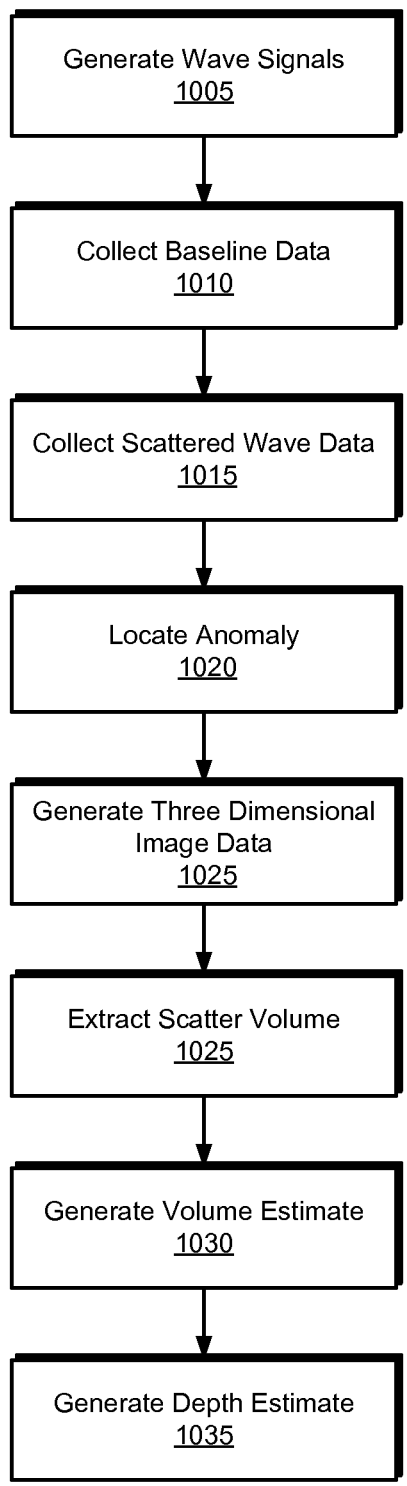
FIG. 10 is a flowchart illustrating operations in a method to characterize an anomaly in a laminate structure, according to embodiments.
Figure 11:
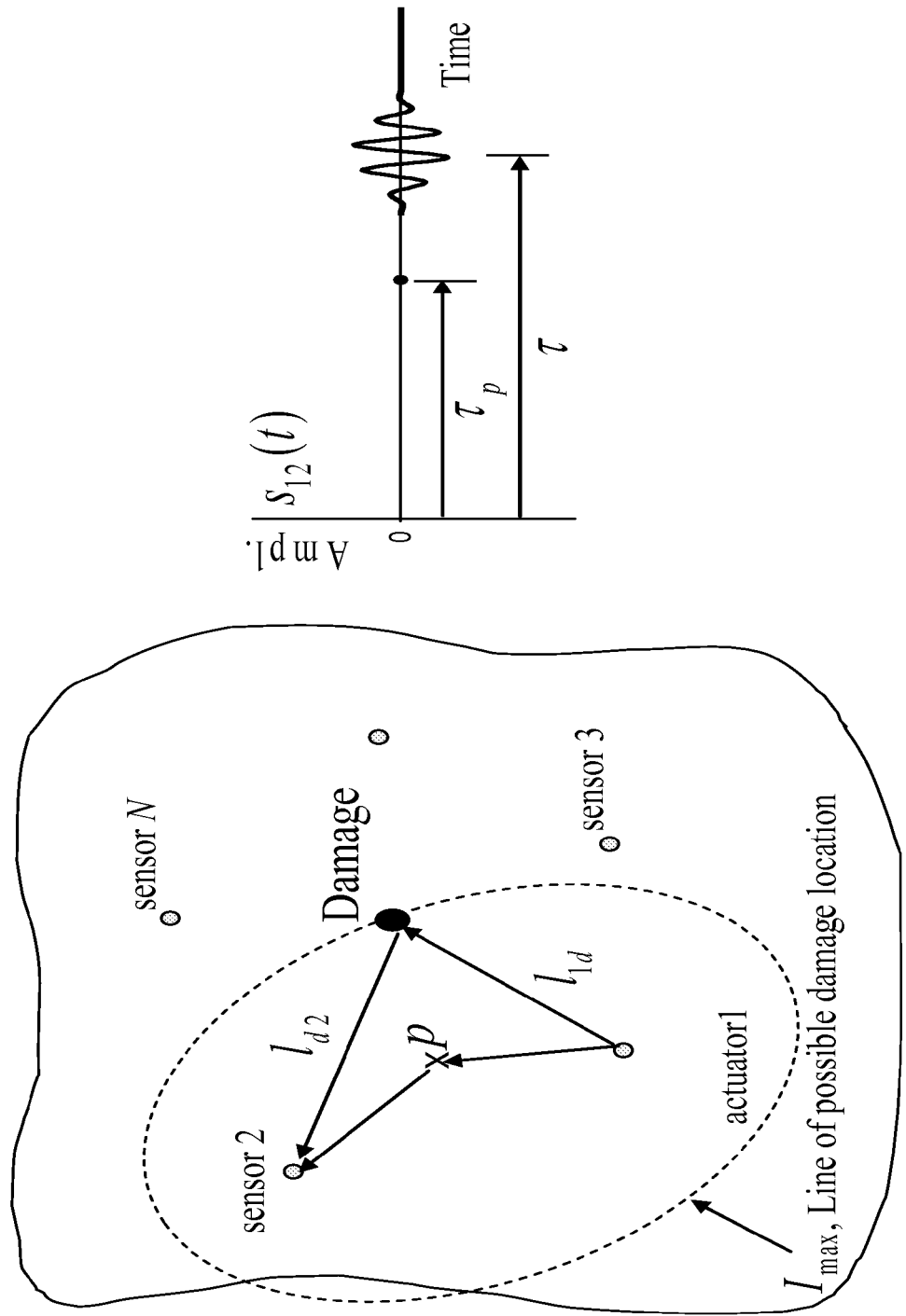
FIG. 11 is a schematic illustration of a sensor arrangement which pinpoints a location of damage in a laminate structure, according to embodiments.

FIG. 10 is a flowchart illustrating operations in a method to characterize an anomaly in a laminate structure, according to embodiments. The general mode of operation is similar to the operation of the system described with reference to FIGS. 1-7. In general, one or more actuator generates waves, which propagate through the laminate and are detected by sensors, which convert the waves to signals. Baseline wave data is collected on an undamaged laminate and may be used to determine one or more parameters associated with wave propagation through the laminate. In one aspect, the system may be used as a damage monitoring system by periodically transmitting waves through the laminate and comparing the signals detected by the sensors to the baseline wave data. In another aspect the system may be used to characterize an anomaly in the laminate. As described above, the system may implement routines to determine a location and size of the laminate. Further, as described below, the system may implement routines to estimate a damage volume and a damage depth.

Referring to FIG. 10, at operation 1005 wave signals are generated in the laminate structure 810. As described above, in some embodiments a pulse wave, lamb wave or similar signal may be generated and directed into a structure being monitored or evaluated. Lamb waves may be used for detecting and determining the size of an anomaly because they are similar to longitudinal waves and include compression and rare fraction but are bounded by the surface of the structure into which they are transmitted causing a wave-guide effect. For easier and more robust imaging process, a single mode of Lamb waves or similar pulse wave (i.e. a0 fundamental asymmetric mode or s0 fundamental symmetric mode) may be injected into a structure.

At operation 1010 baseline wave data for the structure 810 may be collected at a point in time at which the laminate 810 does not have an anomaly. Referring to FIG. 8, for a given set of N distributed sensors (N=6 for the hexagonal pattern depicted in FIG. 8), the response of the healthy structure is collected. In some embodiments the system may implement a round-robin data collection routine, in which a given sensor (i) generates a wave input and the signals are measured at all sensors 1, . . . N. Next, sensor (i+1) generates a wave input and the signals are measured at all sensors 1, . . . N. The process may be repeated until one or more complete data sets including data from all the sensors 820 are included.

As described above with reference to FIG. 2, the baseline wave data may be collected before the laminate structure 810 or object is placed in service or at some point in time before beginning a structural health monitoring program on the laminate structure 810. The baseline wave data may be stored in the baseline wave data module 842, which may be implemented as a file in a computer readable memory module or the like. At operation 1015 scattered wave data is collected.

As described above with reference to FIGS. 1 and 2, scattered wave data is collected from the laminate structure 810 after the anomaly 830 has been generated on the laminate structure 810. When waves are induced in the laminate structure 810, the anomaly 830 scatters the waves which impinge on the anomaly 830. The scattered waves can be decoupled or separated from any other waves by subtracting other reflected waves that are not being reflected from the anomaly, e.g., by subtracting post damage data from pristine (baseline) wave data.

At operation 1020 the anomaly may be located. Consistent with the description provided above, the anomaly 830 may be located by generating one or more multiple ellipses using the scattered data. For example, referring briefly to FIG. 11, a scattered response from an actuator (1) and sensor (2) contains a scattered wave packet arriving at a time τ. The total time delay τ of the scattered wave should correspond to the wave travel time from the actuator 1 to the anomaly and from the anomaly to sensor 2 such that:

$$\tau = \tau_{1d} + \tau_{d2} \qquad \text{Eq. 4}$$

$$\tau_{1d} = l_{1d}/c, \tau_{d2} = l_{d2}/c \qquad \text{Eq. 5}$$

where $l_{1d}$ is the linear distance between the actuator 1 and the anomaly, $l_{d2}$ is the linear distance between the damage and sensor 2, and c is the wave speed. For an unknown anomaly, there are many combinations of $l_{1d}$ and $l_{d2}$ for a given τ. Thus, assuming the wave velocity c is constant, the locus of the anomaly is an ellipse with actuator 1 and sensor 2 as the foci. Multiple ellipses can be generated by assuming damage at arbitrary location p and taking $s_{ij}(\tau_p)$ for actuator i and sensor j such that:

$$\tau_p = \tau_{ip} + \tau_{pj} \qquad \text{Eq. 6}$$

$$\tau_{ip} = l_{ip}/c, \tau_{pj} = l_{pj}/c \qquad \text{Eq. 7}$$

The anomaly 830 may be located by superimposing multiple ellipses generated by multiple sensors substantially as described with reference to FIGS. 7A and 7B, above.

At operation 1025 three dimensional image data for the anomaly 830 is generated. As described above, signal processing is used to convert the raw sensor measurements into smooth waveforms for enhancing the imaging resolution. The raw sensor measurements from sensors 820 can be represented in both time and frequency domains by windowed discrete-time Fourier transform of a signal using a sliding window, i.e., a short time Fourier Transform (STFT).

The STFT of a raw signal s(t) may be defined as:

$$S(\omega, t) = \frac{1}{2\pi} \int_{-\infty}^{\infty} e^{-i\omega\tau} s(\tau) h(\tau - t) d\tau \qquad \text{Eq. 8}$$

Figure 12:
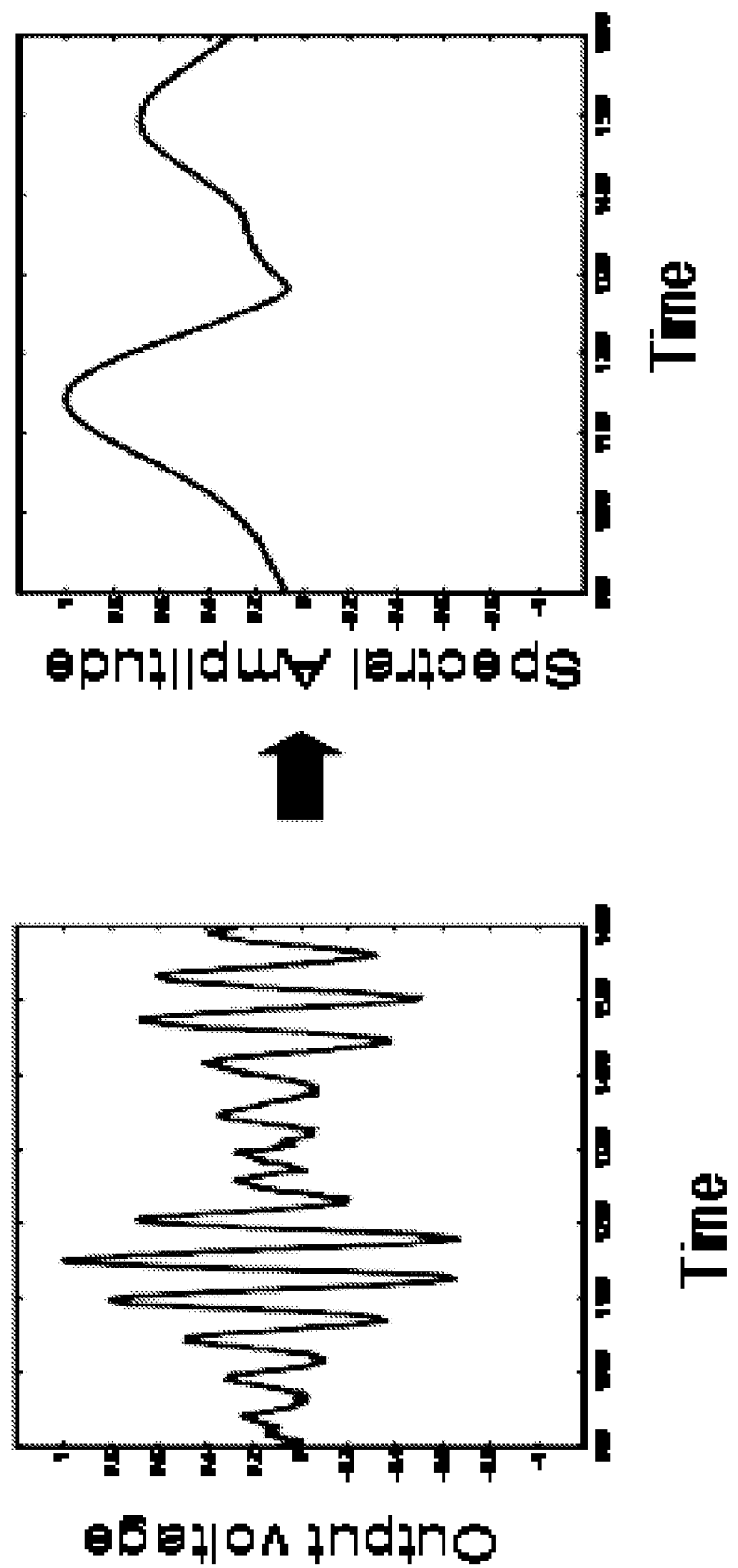
FIG. 12 is a series of graphs illustrating a waveform smoothing function, according to embodiments.
Figure 13:
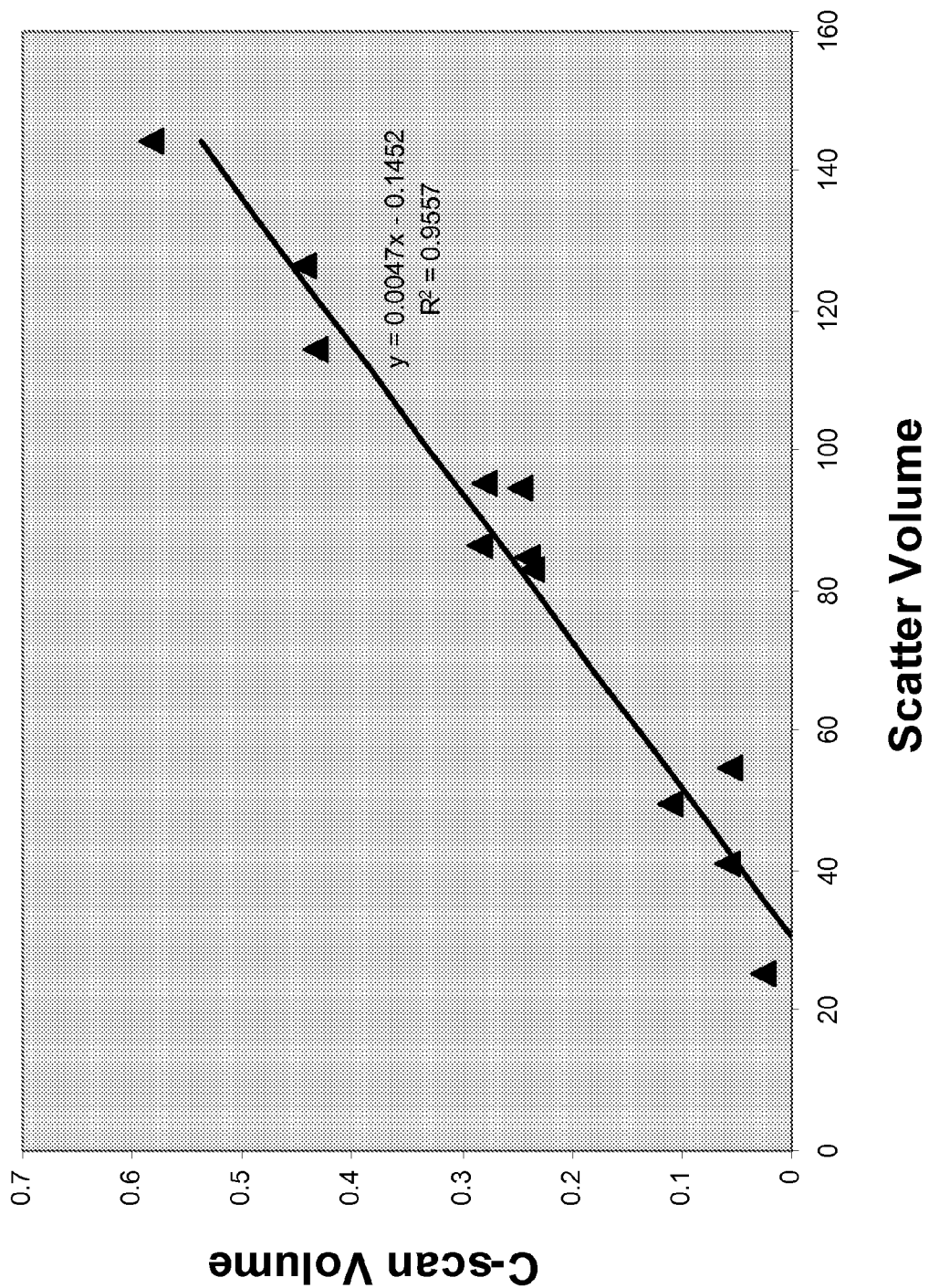
FIG. 13 is a scatter graph plotting the scan volume against the scatter volume, according to embodiments.

Since the window function h(t) has a short time duration, by moving h(t) with Fourier integrals, the signal's local frequency properties evolving over time can be revealed. Instantaneous spectral amplitude over time for a given signal can be obtained by taking the magnitude of s(ω, t) at a driving frequency ω=ω0, which uniquely defines the waveform of the given signal as shown in FIG. 12. Other signal processing techniques could be used for smoothing raw signals and creating an envelop waveform as shown in FIG. 2.

Referring back to FIG. 11, a digital image can then be constructed by relating an illumination value at an arbitrary pixel location I(x,y) to the correlations of the scattered signals received by all diagnostic paths assuming a scatter source (or damage) is located at a location P.

The illumination value I at a pixel location (x,y) using these two approaches is mathematically defined as:

$$I(x, y)|_{\omega=\omega_0} = \sum_{i=1}^{N} \sum_{j=1}^{N} S_{ij}\left(\omega_0, \frac{D}{V_g}\right) \qquad \text{Eq. 9}$$

$$\text{Volume} = \int \int I(x, y) dx dy \qquad \text{Eq. 10}$$

where N is the total number of actuator-sensor paths considered, represents the instantaneous frequency spectrum of the scattered signal, which are received by sensor j due to the excitation of actuator i. D denotes the total geometrical distance from the actuator i to the pixel location I and from the I to the sensor j. Vg refers to the group velocity of the propagating stress wave (fundamental antil symmetric mode) as a function of the excitation frequency ω, and ω0 is the actual excitation frequency used by the actuator i. For highly anisotropic materials, Vg may be also a function of wave propagation angles With the three dimensional illumination data generated, a scatter imaging volume algorithm may be executed to generate three-dimensional image data for the anomaly 830 from the scattered wave data collected in operation 1015. In one embodiment, the scatter volume estimate may be generated (operation 1030) using equation 10.

In some embodiments a non-destructive evaluation technique, referred to as a C-scan process may be used to generate information about the anomaly. The C-Scan process utilizes a transducer head in contact with a part's surface sending an ultrasonic pulse into it. The pulse will be reflected back to the head when it either reaches the other side or when it hits a delamination. The time duration of the reflected pulse is directly related to the depth of damage. Thus, the C-Scan process collects data which defines a cone of damage in the laminate structure. The volume of the damage cone may be estimated by subtracting the volume of the undamaged scan area taken from a scan after impact from the volume of the entire scan area.

Figure 14:
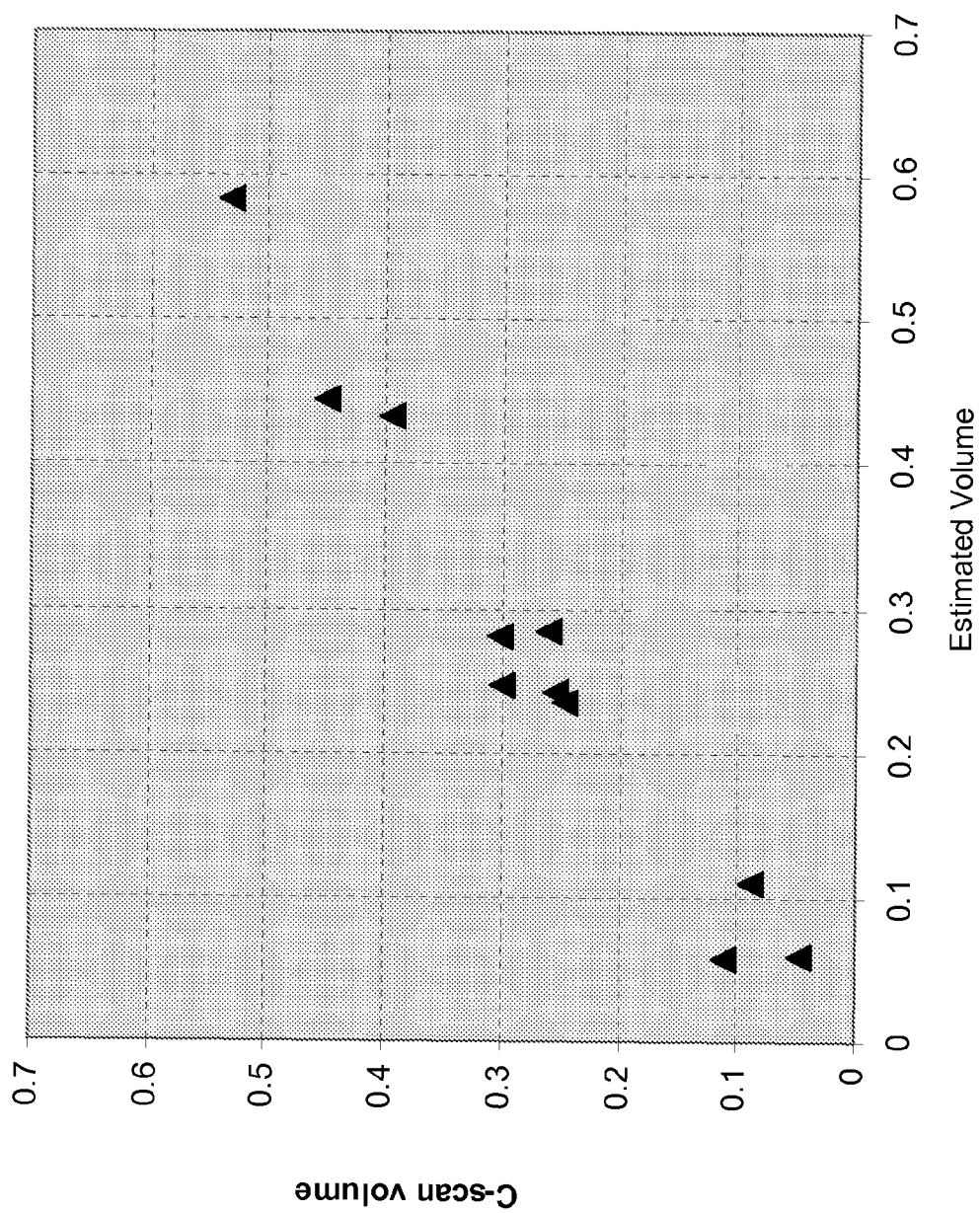
FIG. 14 is a scatter graph which illustrates fitting a curve to a scatter graph, according to embodiments.

Referring now to FIGS. 13-16, in some embodiments a correlation between the scatter volume and the C-Scan volume may be determined. In the embodiment depicted in FIG. 13 a linear correlation (y=0.0047x−0.142) is fit to the data set. However, in other embodiments a different correlation may be established. Thus, the correlation may be used to estimate a C-scan volume from the scatter volume. As illustrated in FIG. 14, a correlation may then be established between the C-scan volume and an estimated volume of the anomaly 830. This linear correlation may be used to relate the scatter volume to a volume of the anomaly 830.

Figure 15:
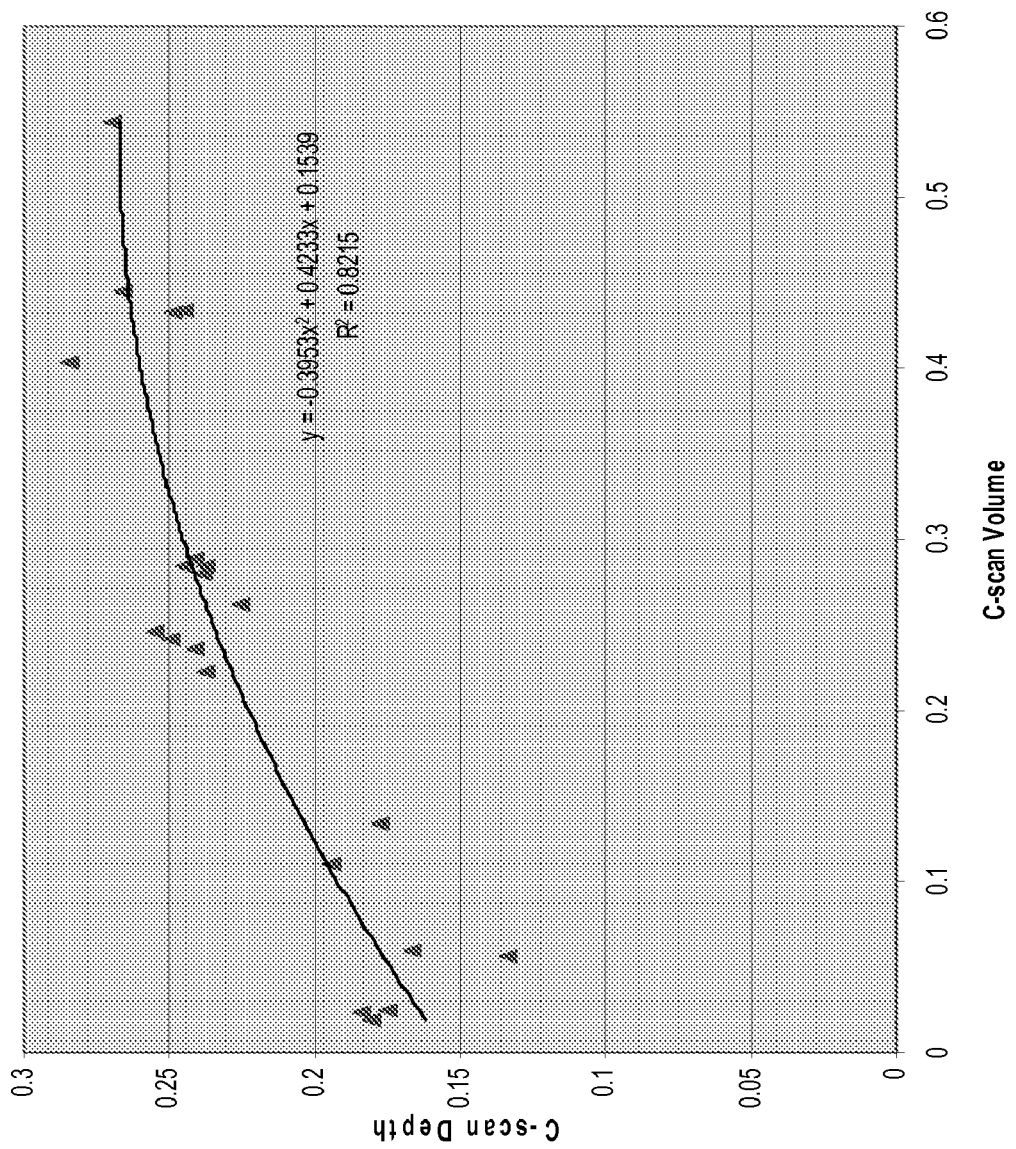
FIG. 15 is a scatter graph plotting the scan depth against the estimated depth, according to embodiments.
Figure 16:
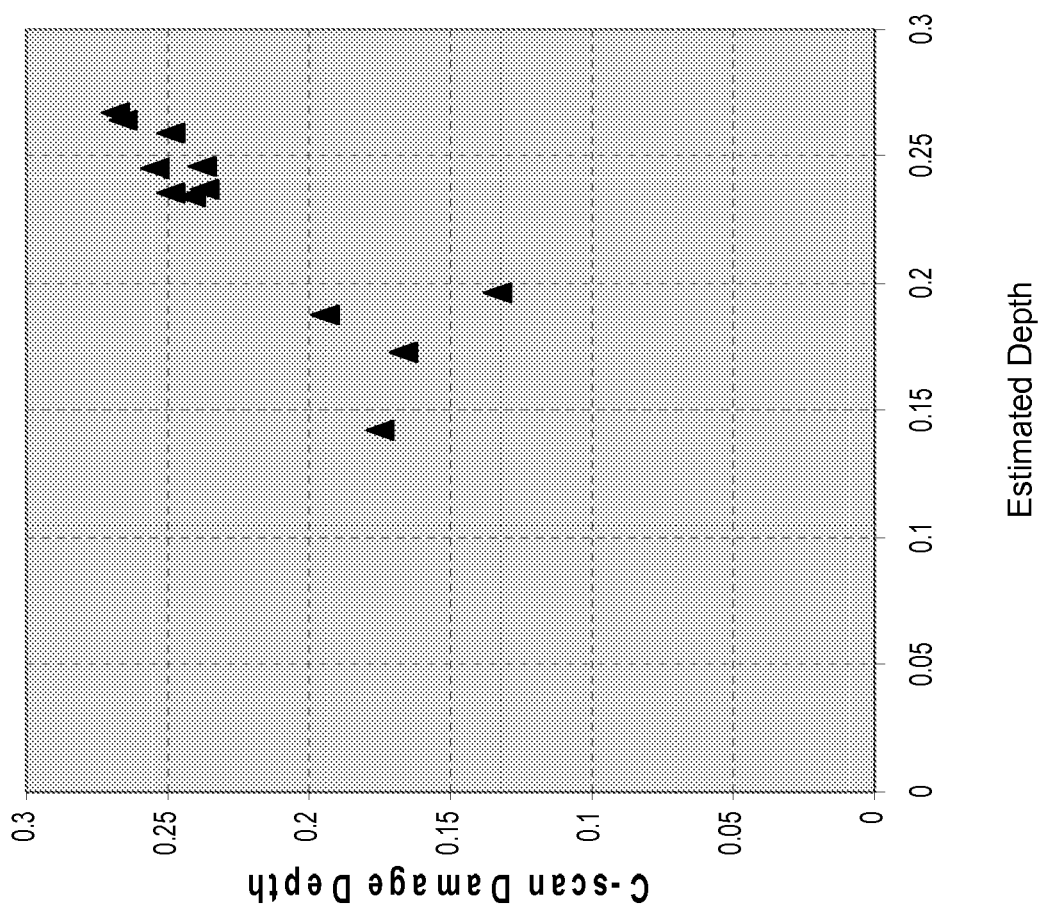
FIG. 16 is a scatter graph which illustrates fitting a curve to a scatter graph of scan volume plotted against scan depth.

Similarly, as illustrated in FIG. 15, a correlation may be established between the C-scan volume and the C-scan depth. In the embodiment depicted in FIG. 15 a quadratic equation (y=0.3953X2+0.4233X+0.1539) is fit to the data set. However, in other embodiments a different correlation may be established. Thus, the correlation may be used to generate an estimate (operation 1035) of a depth of the anomaly 830 from the C-scan damage depth, as illustrated in FIG. 16.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," and "includes" and/or "including" when used in this specification, specify the presence of stated features, integers, steps, operations, elements, and/or components, but do not preclude the presence or addition of one or more other features, integers, steps, operations, elements, components, and/or groups thereof.

Although specific embodiments have been illustrated and described herein, those of ordinary skill in the art appreciate that any arrangement which is calculated to achieve the same purpose may be substituted for the specific embodiments shown and that the invention has other applications in other environments. This application is intended to cover any adaptations or variations of the present invention. The following claims are in no way intended to limit the scope of the invention to the specific embodiments described herein.

Reference in the specification to "one embodiment" or "some embodiments" means that a particular feature, structure, or characteristic described in connection with the embodiment is included in at least an implementation. The appearances of the phrase "in one embodiment" in various places in the specification may or may not be all referring to the same embodiment.

Although embodiments have been described in language specific to structural features and/or methodological acts, it is to be understood that claimed subject matter may not be limited to the specific features or acts described. Rather, the specific features and acts are disclosed as sample forms of implementing the claimed subject matter.

What is claimed is:

1. A method to characterize an anomaly in a laminate structure using a distribution of actuators and sensors, comprising:
generating a series of wave signals in the structure from the distribution of actuators;
collecting, in the sensors, scattered wave data caused by the series of generated wave signals impacting the anomaly;
executing a scatter imaging algorithm to generate three dimensional image data for the anomaly from the scattered wave data;
extracting a scatter volume from the scattered wave data; and
generating a damage volume estimate and a damage depth estimate from the scattered wave data.

2. The method of claim 1, further comprising generating a baseline wave data set for the laminate structure, wherein the baseline wave data set comprises wave data collected from the laminate structure when the laminate structure is undamaged.

3. The method of claim 2, further comprising calibrating a velocity of propagation of waves in the structure by using the baseline wave data.

4. The method of claim 2, further comprising performing signal processing on the scattered wave data the baseline wave data for the structure.

5. The method of claim 1, further comprising using at least one of mode conversion and noise conversion to identify the at least one of front and back scattered waves and side scattered waves and to separate each signal.

6. The method of claim 1, wherein the distribution of actuators and sensors comprises a distribution of piezoelectric sensors, each of which functions as both a actuator and a sensor.

7. The method of claim 6, wherein the actuators and sensors operate in one of a pitch-catch mode and a pulse-echo mode, wherein:
the pitch-catch mode comprises generating a pulse wave by a plurality of the actuators and collecting the scattered wave data in selected sensors, each actuator-sensor pair forming a pitch-catch pulse wave path; and
the pulse-echo mode comprises generating a pulse wave by a plurality of the actuators and collecting the scattered wave data by the same sensor that generated the pulse wave.

8. The method of claim 7, further comprising:
generating a multiplicity of actuator-sensor pulse wave paths to generate the three dimensional image data for the anomaly based at least in part on a time of flight of one or more backscattered waves; and
superimposing the actuator-sensor pulse wave paths on one another over a portion of the structure being evaluated to generate the three dimensional image of the anomaly, wherein a shape of each actuator-sensor pulse wave path is determined by a wave velocity profile as a function of a wave propagation angle and a measured time-of-flight of one or more backscattered waves.

9. The method of claim 8, wherein generating a damage volume estimate comprises determining a correlation between the three dimensional image volume and a damage volume.

10. The method of claim 8, wherein generating a damage depth estimate comprises determining a correlation between the three dimensional image volume and a damage volume.

11. A system to characterize an anomaly in a laminate structure, comprising:
   a plurality of actuators to generate a wave signal into a structure being evaluated;
   a plurality of sensors to collect scattered wave data caused by energy of the wave signal being at least partially reflected or scattered by an anomaly; and
   a structural health monitoring unit to:
      execute a scatter imaging algorithm to generate three dimensional image data for the anomaly from the scattered wave data;
      extract a scatter volume from the from the scattered wave data; and
      generate a damage volume estimate and a damage depth estimate from the scattered wave data.

12. The system of claim 11, wherein the structural health monitoring unit further comprises a module to identify and separate anomaly scattered wave signals from other wave signals.

13. The system of claim 11, wherein the structural health monitoring unit further comprises a module to measure a size of the anomaly from a time-of-flight of at least one scattered wave based on the calibrated velocity of propagation of waves in the structure.

14. The system of claim 11, wherein the structural health monitoring unit comprises a piezoelectric actuator which can function as an ultrasonic wave generator and an ultrasonic wave sensor.

15. The system of claim 11, wherein the structural health monitoring unit further comprises a module to generate a baseline wave data set for the laminate structure, wherein the baseline wave data set comprises wave data collected from the laminate structure when the laminate structure is undamaged.

16. The system of claim 11, wherein the structural health monitoring unit further comprises a module to calibrate a velocity of propagation of waves in the structure by using the baseline wave data.

17. The system of claim 11, wherein the structural health monitoring unit further comprises a module to use at least one of mode conversion and noise conversion to identify the at least one of front and back scattered waves and side scattered waves and to separate each signal.

18. The system of claim 11, wherein the actuators and sensors operate in one of a pitch-catch mode and a pulse-echo mode, wherein:
   the pitch-catch mode comprises generating a pulse wave by a plurality of the actuators and collecting the scattered wave data in selected sensors, each actuator-sensor pair forming a pitch-catch pulse wave path; and
   the pulse-echo mode comprises generating a pulse wave by a plurality of the actuators and collecting the scattered wave data by the same sensor that generated the pulse wave.

19. The system of claim 18, wherein:
   the system generates a multiplicity of actuator-sensor pulse wave paths to generate the three dimensional image data for the anomaly based at least in part on a time of flight of one or more backscattered waves; and
   the structural health monitoring unit comprises a module to superimpose the actuator-sensor pulse wave paths on one another over a portion of the structure being evaluated to generate the three dimensional image of the anomaly, wherein a shape of each actuator-sensor pulse wave path is determined by a wave velocity profile as a function of a wave propagation angle and a measured time-of-flight of one or more backscattered waves.

20. The system of claim 19, wherein the structural health monitoring unit comprises a module to determine a correlation between the three dimensional image volume and a damage volume.

21. The system of claim 19, wherein the structural health monitoring unit comprises a module to determine a correlation between the three dimensional image volume and a damage volume.

* * * * *